United States Patent
Schildkraut et al.

(10) Patent No.: US 11,864,942 B2
(45) Date of Patent: Jan. 9, 2024

(54) METHODS FOR CALIBRATING A SPECTRAL X-RAY IMAGING SYSTEM TO PERFORM MATERIAL DECOMPOSITION

(71) Applicant: CARESTREAM DENTAL LLC, Atlanta, GA (US)

(72) Inventors: Jay S. Schildkraut, Rochester, NY (US); Jean-Marc Inglese, Bussy-Saint-Georges (FR); Krishnamoorthy Subramanyan, Palatine, IL (US); Vincent Loustauneau, Fontenay sous Bois (FR)

( * ) Notice: Subject to any disclaimer, the term of this patent is extended or adjusted under 35 U.S.C. 154(b) by 79 days.

(21) Appl. No.: 17/419,088

(22) PCT Filed: Dec. 27, 2019

(86) PCT No.: PCT/US2019/068853
§ 371 (c)(1),
(2) Date: Jun. 28, 2021

(87) PCT Pub. No.: WO2020/142396
PCT Pub. Date: Jul. 9, 2020

(65) Prior Publication Data
US 2022/0061794 A1 Mar. 3, 2022

Related U.S. Application Data

(60) Provisional application No. 62/786,476, filed on Dec. 30, 2018.

(51) Int. Cl.
*A61B 6/00* (2006.01)
*G01T 1/169* (2006.01)
(Continued)

(52) U.S. Cl.
CPC .............. *A61B 6/584* (2013.01); *G01T 1/169* (2013.01); *G01T 1/36* (2013.01); *G01T 7/005* (2013.01)

(58) Field of Classification Search
CPC .......... A61B 6/584; G01T 1/169; G01T 1/36; G01T 7/005
See application file for complete search history.

(56) References Cited

U.S. PATENT DOCUMENTS

2009/0262997 A1* 10/2009 Zou .................... A61B 6/583
382/131

OTHER PUBLICATIONS

S. I. Miroshnychenko et al. , "Simulated Phantom Projections for Reconstruction Quality Control in Digital Tomosynthesis," 2018 IEEE 38th International Conference on Electronics and Nanotechnology (ELNANO), Kyiv, UKraine, 2018, pp. 406-410, doi: 10.1109/ELNANO.2018.8477526 (Year: 2018).*

* cited by examiner

*Primary Examiner* — Hugh Maupin

(57) ABSTRACT

The present disclosure describes methods for calibrating a spectral X-ray system to perform material decomposition with a single scan of an energy discriminating detector or with a single scan at each used X-ray spectrum. The methods may include material pathlengths exceeding the size of the volume reconstructable by the system. Example embodiments include physical and matching calibration phantoms. The physical calibration phantom is used to measure the attenuation of X-rays passing therethrough with all combinations of pathlengths through the calibration's basis materials. The matching digital calibration phantom is registered with the physical calibration phantom and is used to calculate the pathlength though each material for each measured attenuation value. A created data structure includes the X-ray attenuation for each X-ray spectrum or detector energy bin (Continued)

for all combinations of basis material pathlengths. The data structure is usable to perform a material decomposition on the X-ray projection of an imaged object.

13 Claims, 6 Drawing Sheets

(51) Int. Cl.
 *G01T 1/36* (2006.01)
 *G01T 7/00* (2006.01)

METHODS FOR CALIBRATING A SPECTRAL X-RAY IMAGING SYSTEM TO PERFORM MATERIAL DECOMPOSITION

FIELD OF THE INVENTION

The present invention relates to the field of X-ray imaging and, more particularly, to spectral X-ray systems and scans.

BACKGROUND OF THE INVENTION

Spectral X-ray imaging systems that measure the energy dependence of an object's X-ray attenuation coefficient provide more information about the object's material composition than non-spectral X-ray systems. One United States patent describes an apparatus which images an object with a low and high energy X-ray spectrum to measure an atomic number dependent signal and produce energy dependent X-ray images of an object. The motivation behind this apparatus was to decompose the X-ray image into a photoelectric component which depends strongly on a material's atomic number and a Compton component which depends on a material's electron density. The photoelectric and Compton images provide more information about the material composition of an object as compared with a radiodensity image which is obtained by a non-spectral X-ray system.

Several types of spectral X-ray imaging systems have been proposed and are commercially available. Most spectral X-ray systems use dual-energy in which either a single X-ray source exposes an object with two different X-ray spectra by changing the source voltage and/or filtration. Alternately, two sources with different spectra, each with a corresponding detector may be used. More recently, photon counting detectors have been developed which are able to measure the energy of X-ray photons by assigning a detected photon to two or more energy bins. Spectral X-ray imaging systems can be two-dimensional as in the case of dual-energy X-ray absorptiometry (DEXA) or three-dimensional as in the case spectral fan-beam or cone beam scanners.

A primary application of spectral X-ray imaging systems is to decompose a scanned object into two or more components. As described above, this can be in terms of a photoelectric and Compton component. Alternatively, the components may be two or more basis materials. For the purposes of the present patent application, the present invention is described with respect to example embodiments comprising dual-energy or photon counting detectors with two energy bins and material decomposition into two basis materials. However, it should be understood and appreciated that the present invention applies, in general, to embodiments having more than two X-ray ray spectra, detector energy bins, and basis materials.

Consideration is first given to the case of dual-energy X-ray imaging with source energy spectrum $S_1(E)$ and $S_2(E)$. The relationship between the source X-ray spectra and the X-rays incident on the detector $I_1$ and $I_2$ is given by the X-ray attenuation equations:

$$I_1(A_1,A_2) = \int S_1(E) e^{-A_1 \hat{\mu}_1(E) - A_2 \hat{\mu}_2(E)} dE$$

$$I_2(A_1,A_2) = \int S_2(E) e^{-A_1 \hat{\mu}_1(E) - A_2 \hat{\mu}_2(E)} dE$$

where $A_1$ and $A_2$ are the pathlength times the density (integral density) of the X-rays through basis material 1 and 2, and $\hat{\mu}_1$ and $\hat{\mu}_2$ (add hats) are the energy dependent mass attenuation coefficient of base material 1 and 2. The source energy spectrum may be adjusted to compensate for the spectral sensitivity of the detector.

The X-ray projection of an object is the image on the detector after X-rays from a source have been attenuated by the object. Each pixel of the detector will have a value which depends on the detector type. For example, an energy integrating detector will have pixel values that are proportional to the charge that accumulated on a capacitor during the time of image acquisition. A photon counting detector has pixel values that are related to the number of photons that were detected during image acquisition.

An X-ray projection is decomposed into two basis material images by measuring detector signal $I_1$ and $I_2$ and inverting the attenuation equations to obtain $A_1$ and $A_2$. In the case of a tomographic system such as a cone beam scanner, the values of $A_1$ and $A_2$ for a set of projections can be back-projected to obtain a three-dimensional image of the basis material densities $\rho_1$ and $\rho_2$ of a scanned object.

The basis materials are selected to be representative of the types of materials that are expected in a scanned object. For example, in medical and dental applications, the scanned object consists mostly of soft tissues and bone. Also, implants that are made of metal and other material may be present. One choice of basis materials are average soft tissue and hydroxyapatite, the mineral in bone. Another, possible choice of basis materials is water and metal. The choice of basis materials depends on the spectral X-ray imaging application. It is not necessary that an object actually be a mixture of the basis materials for material decomposition to work. Material decomposition indicates how much a material resembles a basis material in terms of its X-ray attenuation.

In order to perform a material decomposition, the dual-energy attenuation equations must be inverted to obtain the integrated densities $A_1$ and $A_2$ from the measure values of hand $I_2$. This can be accomplished, for example, by using a known method if the X-ray spectra and detector spectral sensitivity are known. Methods exist to calculate the X-ray source spectrum based on the source voltage, filtration and other characteristics. Also, the detector spectral response can be calculated if the detector's properties are known. However, often the exact source and detector properties are unknown. Furthermore, the mass attenuation coefficient of the basis materials as a function of energy can be calculated if the composition of these materials is known, but often this is not the case.

For these reasons, it is desirable to perform an empirical calibration of a dual-energy scanner which enables a projection to be decomposed into the basis materials images without complete knowledge of the characteristics of the X-ray source, X-ray detector, and basis materials. One European patent provides a method for calibrating a dual-energy CT system by pre-creating a look-up-table that contains the low and high energy spectrum attenuation for different combinations of pathlengths through the two basis materials. This calibration procedure requires multiple X-ray attenuation measurements for a range of thickness combinations of the two basis materials.

Based on the foregoing, it would be desirable to have a method for empirically calibrating a spectral X-ray system for a range of pathlengths that exceed the dimension of an object that can be reconstructed by the system. For example, to minimize dose to the patient, dental cone beam scanners are designed so that only a volume-of-interest (VOI) is irradiated for all acquired projections. System calibration is hampered because this VOI is often much smaller than the size of a calibration phantom which is required to provide calibration data for the range of material pathlengths of X-rays passing thought an object such as a human head. For example, to calibrate a system to perform material decomposition of a human head requires a pathlength of at least 20 cm for a soft tissue-like basis material and 3 cm for a bone-like basis material.

It would also be desirable to have a method for empirically calibrating a spectral X-ray system to perform material decomposition that requires only one scan of a calibration phantom at each of the spectra or a single scan with an energy resolving detector. This may be accomplished by providing a method to correct the acquired projections for scatter so that it is not necessary to scan small sections of a calibration phantom at a time to minimize scatter.

There is, therefore, a need in the industry for apparatuses and methods for calibrating a spectral X-ray system to perform material decomposition of a scanned object that solves the problems, difficulties, and shortcomings of already existing apparatuses and methods described herein, that provides the desired methods described herein, and that provides other desirable features and methods.

SUMMARY OF THE INVENTION

Broadly described, the present invention comprises apparatuses and methods for calibrating an X-ray system to perform material decomposition with a single scan in the case of an energy discriminating detector or with a single scan at each X-ray spectrum that is used by the system. The methods may include material pathlengths which exceed the size of the volume that the system can reconstruct. According to example embodiments described herein and without limiting the scope of the present invention, the example embodiments include both a physical calibration phantom and a matching digital calibration phantom. The physical calibration phantom (also sometimes referred to herein as the "physical phantom") is used to measure the X-ray attenuation of rays which pass through the physical calibration phantom with all combinations of pathlengths through the basis materials which need to be included in the calibration. The matching digital calibration phantom (also sometimes referred to herein as the "digital phantom") is registered with the physical calibration phantom and is used calculate the pathlength though each material for each measure attenuation value. Additionally, the registered digital calibration phantom is used in a simulation in which the scatter in the acquired projections is calculated. The calculated scatter is used to scatter correct the acquired projections.

Advantageously, according to the present invention's methods of calibration, a data structure can be created which includes the X-ray attenuation for each X-ray spectrum or detector energy bin for all combinations of basis material pathlengths. The data structure can then be used in accordance with the methods to perform a material decomposition on the X-ray projection of an object which is imaged by the spectral X-ray system.

Also, it should be noted that the present invention is applicable to energy discriminating photon counting detectors for which response may depend on the intensity of the photon flux. This is because coincident photons may only be recorded once because of dead time or alternatively, coincident photons may be assigned to the wrong energy bin. The response of this type of detector is dependent on material pathlengths because the pathlengths determine the intensity of the X-ray irradiation at the detector. Since the calibration methods of the present invention include the measurement of the detector signal throughout the full range of photon intensities at the detector, non-ideal detector characteristics are corrected.

In addition to the above-described inventive apparatuses, methods, and advantages of the present invention, other inventive apparatuses, methods, and advantages of the present invention will become apparent from the description and accompanying drawings of example embodiments of the present invention included herein.

BRIEF DESCRIPTION OF THE DRAWINGS

FIG. 5a displays a schematic representation illustrating the acquisition of a projection of the physical calibration phantom in accordance with the example embodiments of the present invention.

FIG. 5b displays a schematic representation illustrating the acquisition of another projection of the physical calibration phantom in accordance with the example embodiments of the present invention and in which the imaging system's X-ray source and detector are at locations different than in FIG. 5a.

DETAILED DESCRIPTION OF THE EXAMPLE EMBODIMENTS

Figure 1:
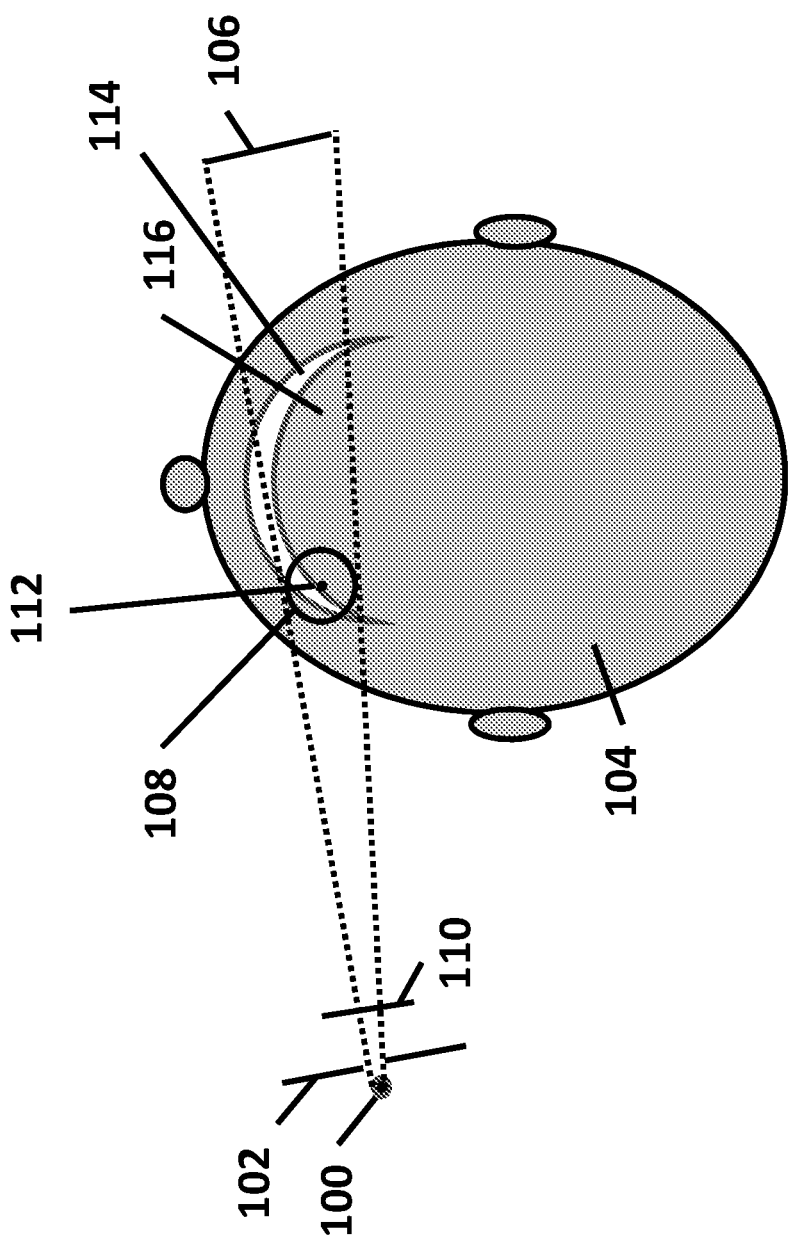
FIG. 1 displays an X-ray imaging system irradiating a patient's head in accordance with the example embodiments of the present invention.

Referring now to the drawings in which like numerals represent like elements or steps throughout the several views, FIG. 1 displays a focal spot of an X-ray source 100 of an X-ray imaging system irradiating a patient's head 104 in accordance with the example embodiments of the present invention. It should be understood and appreciated that while the present description refers to a patient's head 104 as the object being irradiated by the X-ray imaging system, such irradiation could include other parts of a patient's body or, simply, other objects. X-rays emitted by the X-ray source 100 are collimated by collimator 102 so that the X-rays are limited to the area of a detector 106. The X-rays can also pass through a filter 110 before entering the patient or other object. When an X-ray scan is acquired, the X-ray source 100, the collimator 102, the filter 110, and the detector 106 are moved around the patient. Typically, the X-ray source 100 is moved in a circle around a fixed point 112, which is often referred to as the isocenter or axis of rotation (AOR). Generally, for 3D image reconstruction, the X-ray source 100 and detector 106 need to traverse an angular range of 180 degrees plus the fan beam angle. A volume-of-interest (VOI) 108 is the volume of the patient 104 (or other object) that is irradiated by the X-ray source 100 at all source focal spot locations of the X-ray scan. The VOI 108 may be fully reconstructed into a 3D image whereas the region of the patient 104 (or other object) outside of this VOI 108 may only be partially reconstructed, and generally with distorted geometry.

For the purpose of the present description, the patient's head 104 is considered to include soft tissue basis material 114 (such as, for example and not limitation, the patient's skin or gums) and bone basis material 116 (such as, for example and not limitation, the patient's maxillary or mandibular jaw bones). As illustrated in FIG. 1, X-rays travel from a source focal spot of an X-ray source 100 to a pixel on detector 106 and the pathlength (distance traveled) through both of the basis materials 114, 116 exceeds the dimension of the reconstructed VOI 108. Therefore, any calibration phantom which comprises the two basis materials needs to include pathlengths through one or both of the basis materials which exceed the size of the volume that the system can reconstruct.

Figure 2:
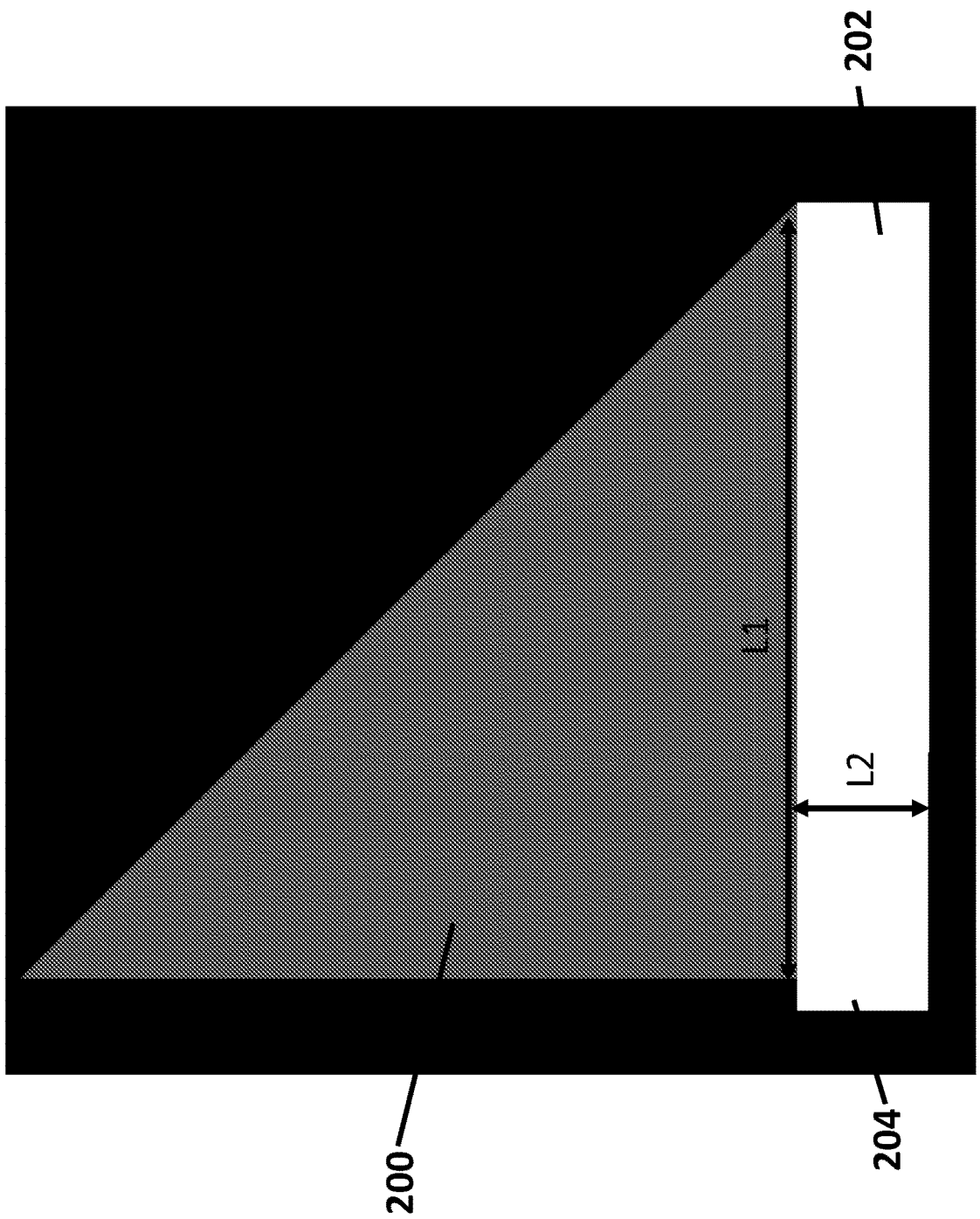
FIG. 2 displays a material decomposition calibration phantom in accordance with the example embodiments of the present invention.

FIG. 2 displays the material decomposition calibration phantom according to the example embodiments of the present invention. As illustrated in FIG. 2, a wedge 200 of basis material 1 is attached to wedge 202 of basis material 2. Wedge 200 has length L1 which is the maximum pathlength that is calibrated for basis material 1 and wedge 202 has a length L2 which is the maximum pathlength that can be included in the calibration for basis material 2. Wedge 202 has overhang 204 to provide pathlengths of only basis material 2.

Figure 3:
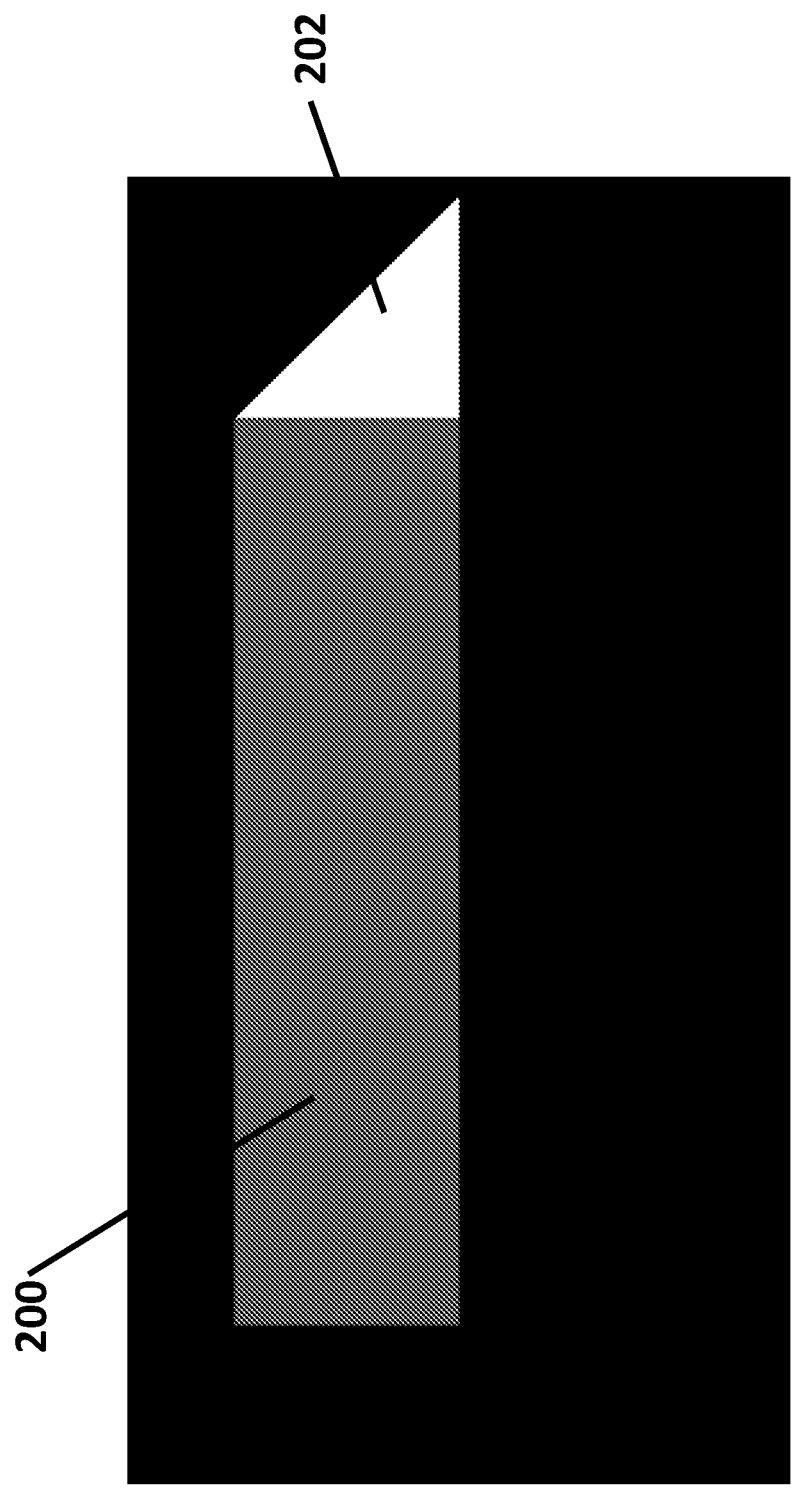
FIG. 3 displays a side view of the material decomposition calibration phantom in accordance with the example embodiments of the present invention.

FIG. 3 displays a side view of the material decomposition calibration phantom according to the example embodiments of the present invention. In FIG. 3, the shape of wedge 202 is apparent.

Figure 4:
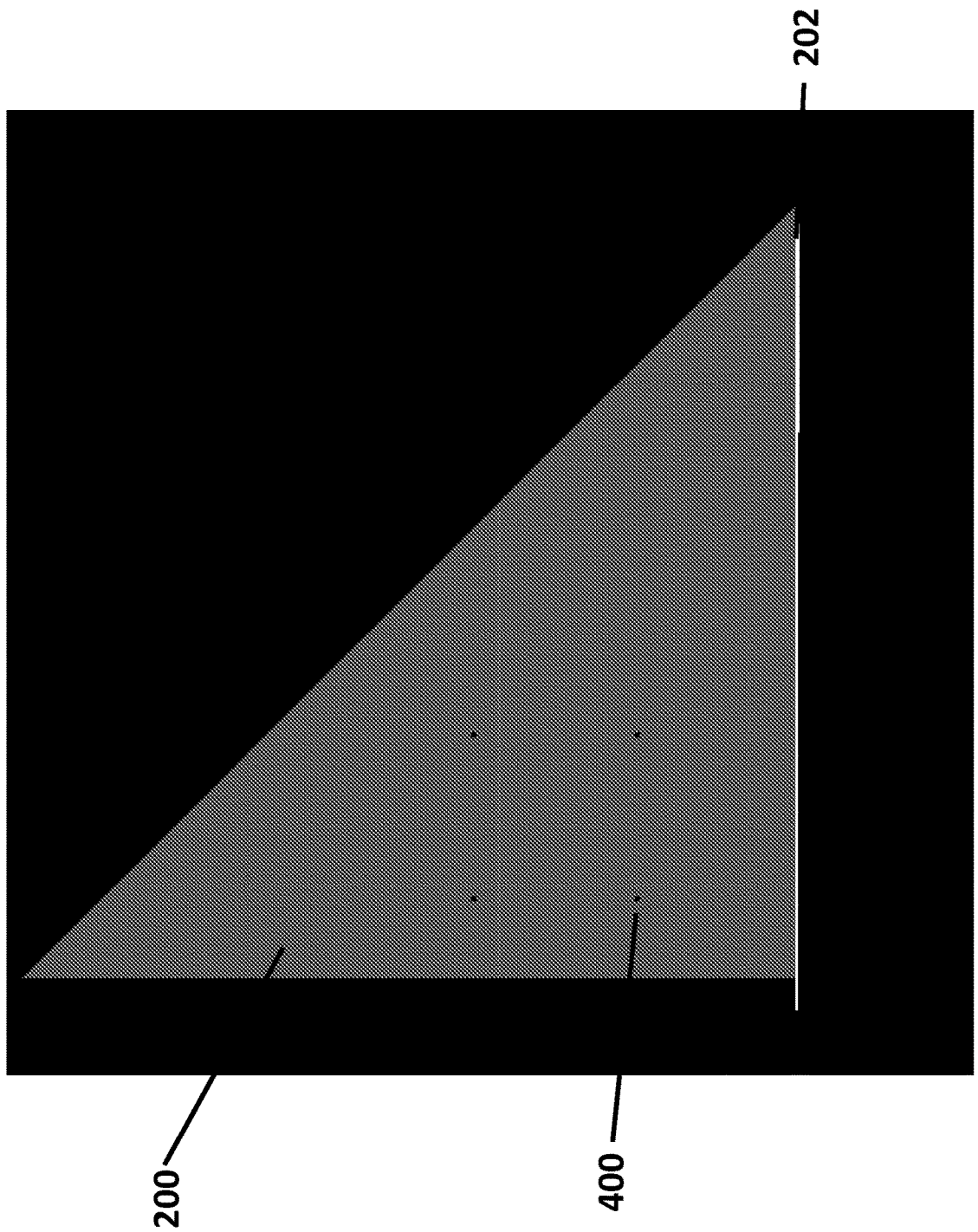
FIG. 4 displays a top view of the material decomposition calibration phantom in accordance with the example embodiments of the present invention.

FIG. 4 displays a top view of the material decomposition calibration phantom according to the example embodiments of the present invention and in which alignment markers 400 visible. The alignment markers 400 are used to register a reconstruction of the physical phantom with the corresponding digital phantom as described below.

Figure 5:
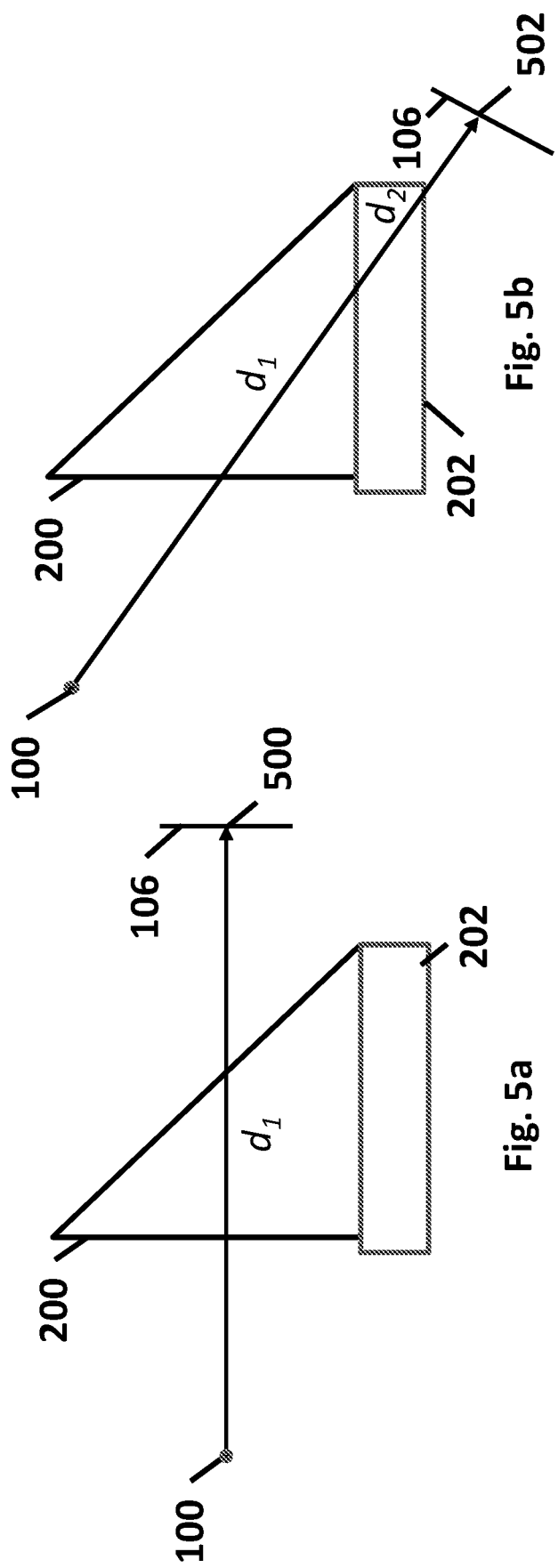

FIG. 5a displays a schematic representation illustrating the acquisition of a projection of the physical phantom according to the example embodiments of the present invention. As illustrated in FIG. 5a, an X-ray travels from X-ray source 100 to pixel 500 on detector 106. The pathlength through basis material 1 is $d_1$. The attenuation at pixel 500 is often expressed as $-\log(I/I_0)$, where I is the measured signal and $I_0$ is the signal of the unattenuated X-ray when the phantom is absent.

FIG. 5b displays, according to the example embodiments of the present invention, a schematic representation illustrating the acquisition of another projection of the physical phantom with X-ray source 100 and detector 106 at locations different than their respective locations in FIG. 5a. In this case, detector pixel 502 measures the attenuation of an X-ray as it travels from the source to detector passing through pathlength $d_1$ of basis material 1 and $d_1$ of basis material 2. When a set of projections is acquired of the physical phantom over a range of source and detector locations it is possible to obtain the attenuation of an X-ray for all combinations of pathlengths through basis material 1 and 2 from zero to the pathlength L1 and L2 (see FIG. 2) for basis material 1 and 2, respectively.

Figure 6:
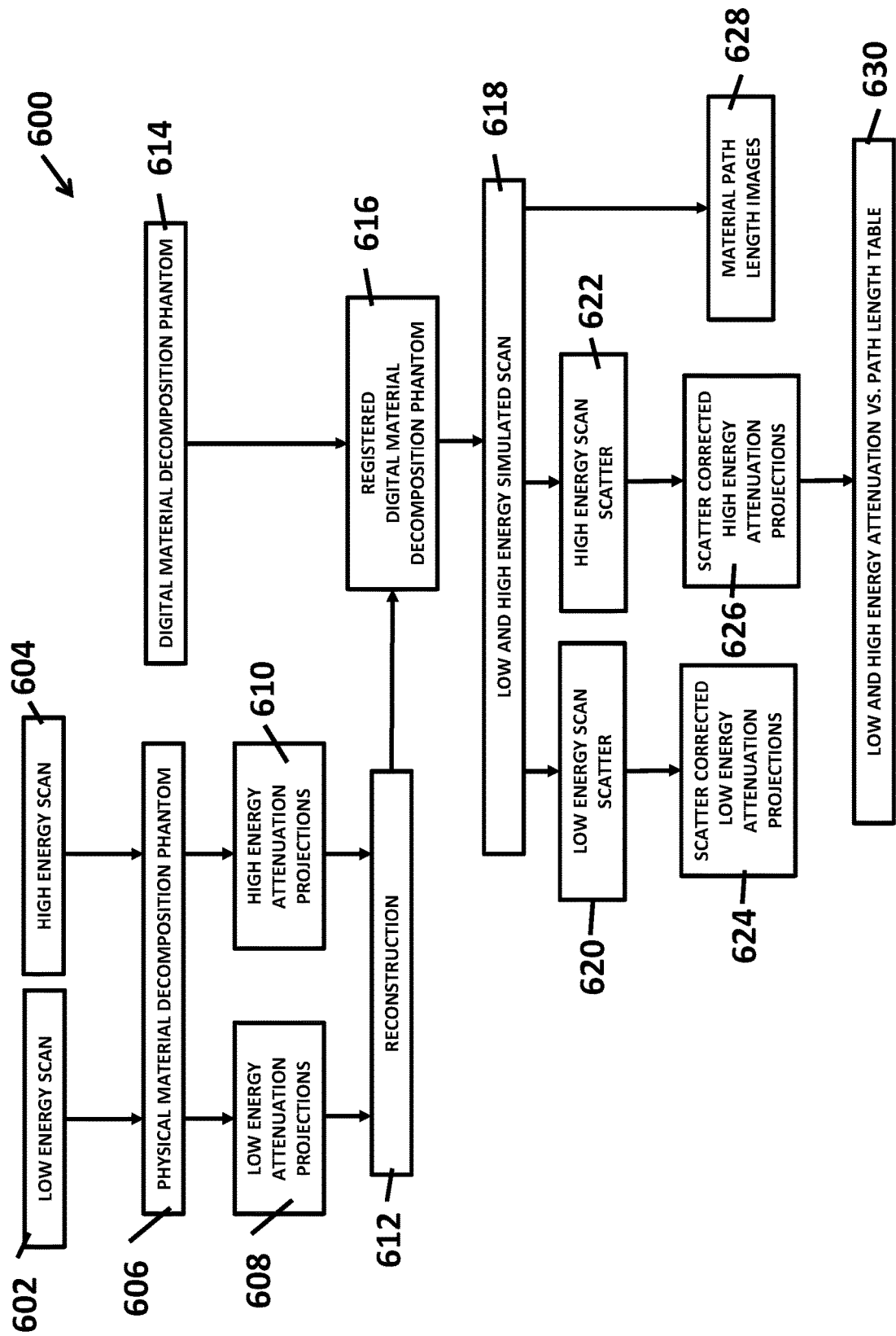
FIG. 6 displays a flowchart representation of a calibration method of the present invention in accordance with the example embodiments and in the context of a dual-energy scan.

FIG. 6 displays a flowchart representation of a method 600 for calibrating a spectral X-ray imaging system to perform material decomposition (also sometimes referred to herein as "calibration method 600") according to the example embodiments of the present invention and in the context of a dual-energy scan. The calibration method 600 begins at steps 602, 604 with the respective acquisition of low and high energy scans of the VOI of the patient 104. In various example embodiments of the present invention, the low energy scan and high energy scan may obtained by two separate scans, by a low and high spectrum energy set of projections within a single scan, or via the low and high energy bins of an energy resolving detector. Next, at step 606, the physical calibration phantom is scanned and a set of low and high energy attenuation projections are, respectively, produced at steps 608 and 610.

At this point in the calibration method 600, the attenuation for the low and high energy scans has been measured. Next, it is necessary to determine the pathlength through the basis materials which corresponds to the low and high energy attenuation value for each pixel of the detector 106. According to the example embodiments, the present invention overcomes difficulties with this part of the calibration method 600 by proving a digital phantom which corresponds to the physical phantom. To understand why this is necessary, consider the possibility of reconstructing the projections from either the low or high energy scans or a combination of the two sets of projections to create a reconstruction at step 612. It is known in the art how to simulate an X-ray acquisition by calculating how a simulated X-ray is attenuated as it propagates from the source (usually modeled as a point) to a detector pixel. In this ray propagation (forward projection) process, it is conceivable that the pathlength through the basis materials could be recorded. In this case, the X-ray attenuation which is related to $I_1$ and $I_2$ and integrated densities $A_1$ and $A_2$ (pathlength x density) are known which allows a table to be constructed that can be used to convert measured values of $I_1$ and $I_2$ to values of $A_1$ and $A_2$. Subsequently, the $A_1$ and $A_2$ values can be back-projected to produce a reconstruction on terms of the basis material densities $\rho_1$ and $\rho_2$.

However, there are this problems with this approach. The reconstruction generally has beam hardening artifacts. Even worse, it is often desirable for one of the basis materials to be a highly attenuating material such as bone or metal. In this case, the reconstruction at step 612 will have what are generally referred to as metal artifacts, but can have problems caused by any material that lowers the X-ray flux to cause photon starvation. These artifacts make it difficult, if not impossible, to determine material type in the forward projection calculation and, hence, to determine material pathlengths.

An even bigger problem is that the pathlengths that are required to be included in the calibration may far exceed the size of the reconstructed volume. The size of the reconstructed volume is determined by the region in space that is irradiated by X-ray for all acquired projections. This is a function of the size of the detector and the distance between the detector and the source. For many scanners the size of the reconstruction is far smaller than the maximum pathlength that an X-ray travels in an object of interest. For example, pathlengths though soft tissue in a patient's head may exceed 20 cm and bone pathlengths may be greater than several centimeters.

In the example embodiments, the present invention solves this problem by providing digital phantom at step 614 which has identical dimensions and composition as the physical phantom reconstructed at step 612. At step 616 of the calibration method 600, the digital phantom is registered to physical phantom. This registration step 616 is facilitated by marks 400, but this registration step 616 is possible even without the use of marks 400.

Continuing at step 618, the registered digital phantom is used to simulate the low and high energy scans obtained at steps 602 and 604. Note that using the digital phantom in this step, instead of the reconstruction of the physical phantom solves the previously described problems with reconstruction artifacts and size limitation. The result of step 618 includes the pathlength through the two basis materials for every X-ray in the scan. For each projection in the scan, two corresponding images are produced at step 628. One image records the pathlength through basis material 1 for a ray from a source focal spot of X-ray source 100 to each pixel on detector 106. The other image does the same for basis material 2. Included in step 618 is a simulation which calculates, at steps 620 and 622, the scatter in the low and high energy spectrum projections. This is typically done using Monte Carlo calculations that model the propagation of X-ray photons through materials. The calculated scatter is then subtracted from the measured projections from steps 608 and 610 to produce scatter corrected low and high energy projections, respectively, at steps 624 and 626.

Finally, at step 630 of the calibration method 600, the basis material pathlength images from step 628 and scatter corrected attenuation projections from steps 624 and 626 are used to create a data structure which contains the low and high energy X-ray spectrum attenuation for all combinations of basis material 1 and 2 pathlengths. The pathlengths range from zero to the value of L1 for material 1 and L2 for material 2.

As a result of the calibration method 600 described with respect to FIG. 6, the set of projection for the scan of an object can be converted into pathlength (or integrated density) images. Upon back-projection, the basis material densities $\rho_1$ and $\rho_2$ of the object are obtained.

The calibration method 600 of the present invention is applicable to a tomographic imaging system which acquires a set of projections and creates three-dimensional reconstructions. In such an example embodiment, the scan of the physical calibration phantom in the calibration method is similar to the scan of an object or patient when the system is in use. It should be understood and appreciated, however, that the present invention may be used in other example embodiments. The source and detector may be incorporated into a scanner which acquires a set of projections over a range of source and detector locations for use with the present calibration method 600. Typically, however, only a single or small number of projections are usually acquired and material decomposition of the projections is thus enabled by the calibration method 600 of the present invention.

In one example embodiment of the present invention, an energy discriminating photon counting detector is used. The calibration method 600 can be simplified by placing the physical calibration phantom on a moving stage (e.g., a rotating stage) such that a scan may be acquired with the source and detector remaining stationary. This calibration fixture is of value in the case that the intended use of the system is to capture a small number of projections.

In a preferred example embodiment of the present invention, an intraoral energy discriminating photon counting detector is calibrated by use of a calibration fixture in which the detector and source remain fixed and the physical phantom is rotated. The calibration method 600 of the present invention allows a data structure to be produced that can be used to transform or convert measured attenuation values versus basis material pathlength. As a result, the images from the intraoral detector can be decomposed, for example, to produce tooth/bone only images and gum only images. In another example embodiment of the present invention, several intraoral images are acquired for the purpose of combined tomosynthesis reconstruction with material decomposition.

In all cases, the images that result from the material decomposition which is enabled by calibration method 600 may be used for viewing or as input for other processing including, without limitation, segmentation, classification, quantification of physical properties including dimension, location, and density.

While the present invention has been described herein with respect to particular example embodiments, it should be understood and appreciated that the scope of the present invention shall not be limited by such example embodiments.

What is claimed is:

1. A method for calibrating a spectral X-ray scanner comprising the steps of:
   a) acquiring projections of a physical phantom at two or more X-ray spectra;
   b) reconstructing the acquired projections of the physical phantom;
   c) making a digital phantom that is a representation of the physical phantom;
   d) registering the digital phantom with said reconstruction; and
   e) using the registered digital phantom in a simulation of the capture of the acquired projections.

2. The method of claim 1, wherein in the simulation of the capture of the acquired projections, the method includes a step of calculating a pathlength of X-rays through a material of the physical phantom.

3. A method for calibrating a spectral X-ray scanner comprising the steps of:
   a) acquiring projections of a physical phantom at two or more X-ray spectra;
   b) reconstructing the acquired projections of the physical phantom;
   c) making a digital phantom that is a representation of the physical phantom;
   d) registering the digital phantom with said reconstruction; and
   e) using the registered digital phantom in a simulation of the capture of the acquired projections,
wherein in the simulation of the capture of the acquired projections, the method includes a step of calculating the X-ray scatter.

4. The method of claim 3, wherein the method further comprises a step of using the calculated X-ray scatter to scatter correct the acquired projections.

5. The method of claim 2, wherein the calculated pathlength is associated with an X-ray attenuation value of the physical phantom as measured by the acquired projections.

6. The method of claim 1, wherein the acquired projections of the physical phantom at two or more X-ray spectra correspond to energy bins of a photon counting detector.

7. The method of claim 2, wherein the method further comprises creating a data structure that associates the X-ray pathlength through two or more materials with the attenuation for two or more X-ray spectra.

8. The method of claim 7, wherein the method further comprises a step of performing a material decomposition of a scanned object through use of the data structure.

9. The method of claim 3, wherein in the simulation of the capture of the acquired projections, the method includes a step of calculating a pathlength of X-rays through a material of the physical phantom.

10. The method of claim 9, wherein the calculated pathlength is associated with an X-ray attenuation value of the physical phantom as measured by the acquired projections.

11. The method of claim 9, wherein the method further comprises creating a data structure that associates the X-ray pathlength through two or more materials with the attenuation for two or more X-ray spectra.

12. The method of claim 11, wherein the method further comprises a step of performing a material decomposition of a scanned object through use of the data structure.

13. The method of claim 3, wherein the acquired projections of the physical phantom at two or more X-ray spectra correspond to energy bins of a photon counting detector.

* * * * *